(12) United States Patent
Okechukwu et al.

(10) Patent No.: US 12,140,518 B2
(45) Date of Patent: Nov. 12, 2024

(54) SAMPLE PREPARATION PRESSURE-VOLUME-TEMPERATURE (PVT) CELL FOR VISCOSITY SAMPLE PREPARATION WITH ELECTROMAGNETIC VISCOMETER (EMV)

(71) Applicant: SAUDI ARABIAN OIL COMPANY, Dhahran (SA)

(72) Inventors: Egbukole Okechukwu, Dhahran (SA); Fawaz M. Al-Otaibi, Dhahran (SA); Daryl Sean Sequeira, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 18/185,084

(22) Filed: Mar. 16, 2023

(65) Prior Publication Data

US 2024/0310263 A1 Sep. 19, 2024

(51) Int. Cl.
*E21B 49/08* (2006.01)
*G01N 11/16* (2006.01)
*G01N 11/00* (2006.01)

(52) U.S. Cl.
CPC .............. *G01N 11/16* (2013.01); *E21B 49/08* (2013.01); *G01N 2011/0086* (2013.01)

(58) Field of Classification Search
CPC .. G01N 11/16; G01N 2011/0086; E21B 49/08
See application file for complete search history.

(56) References Cited

U.S. PATENT DOCUMENTS 2,977,790 A * 4/1961 Dubsky .................. G01N 11/14
73/54.35
8,797,517 B2 8/2014 Karnes et al.
(Continued)

FOREIGN PATENT DOCUMENTS

CN 110646567 A 1/2020
CN 113567302 A 10/2021

OTHER PUBLICATIONS

Gusler, W. et al.; "A New Extreme-HP/HT Viscometer for New Drilling-Fluid Challenges"; SPE Drilling & Completion, Jun. 2007, pp. 81-89 (9 pages).
(Continued)

*Primary Examiner* — Taras P Bemko
(74) *Attorney, Agent, or Firm* — Osha Bergman Watanabe & Burton LLP

(57) ABSTRACT

A system and methods are disclosed. The system includes a temperature control chamber with a temperature system to alter and monitor a temperature of the temperature control chamber and an electromagnetic viscometer (EMV) inside the temperature control chamber to measure a viscosity of a fluid. The system also includes a sample preparation cell within the temperature control chamber pressurized by a constant displacement pump outside the temperature control chamber. The sample preparation cell includes a stirrer; a first valve between a fluid supply reservoir and the sample preparation cell; a second valve between the sample preparation cell and the EMV, a venting fluid line between the sample preparation cell and a gas capturing system, and a venting fluid line to remove released gases from the sample preparation cell. The system further includes a controller to operate the sample preparation cell, temperature system, and EMV.

15 Claims, 7 Drawing Sheets

(56) References Cited

U.S. PATENT DOCUMENTS

| | | |
|---|---|---|
| 10,132,164 B2 | 11/2018 | Dumont et al. |
| 2012/0127466 A1* | 5/2012 | Karnes ............... G01N 33/2811 |
| | | 356/319 |
| 2013/0019663 A1* | 1/2013 | Mendoza De La Cruz ................ |
| | | G01N 11/08 |
| | | 73/54.01 |
| 2016/0040533 A1 | 2/2016 | Harrison et al. |
| 2017/0276584 A1* | 9/2017 | Ye ........................... E21B 21/08 |
| 2020/0182852 A1* | 6/2020 | Stewart .................... G01N 9/36 |
| 2021/0088499 A1* | 3/2021 | Stewart ................. E21B 49/088 |

OTHER PUBLICATIONS

Eakin, B. E. et al.; "Improved High Pressure Capillary Tube Viscometer"; Petroleum Transactions, vol. 216, No. 1, Dec. 1959, pp. 85-91 (7 pages).

ASTM International; "Standard Test Method for Kinematic Viscosity of Transparent and Opaque Liquids (and Calculation of Dynamic Viscosity)1"; Designation: 71/1/97, May 2021, D 445-06 (10 pages).

\* cited by examiner

SAMPLE PREPARATION PRESSURE-VOLUME-TEMPERATURE (PVT) CELL FOR VISCOSITY SAMPLE PREPARATION WITH ELECTROMAGNETIC VISCOMETER (EMV)

BACKGROUND

Oil and gas extraction from subsurface rock formations requires the drilling of wells using drilling rigs mounted on the ground or on offshore rig platforms. Once drilled, the wells may access hydrocarbon reservoirs. Reservoir characterization, such as assessments of reservoir quality, are typically performed using one or more models of the subsurface over a region of interest containing the reservoir.

Obtaining accurate and repeatable dynamic viscosity measurements of reservoir fluids at reservoir temperature and set pressures is important to reservoir fluid studies. The viscosity data aids in evaluating fluid behaviors and decisions on fluid transport mechanisms and the design of flow lines.

The conventional high temperature and pressure viscometers currently used in the oil and gas industry for dynamic viscosity measurements of reservoir fluids have typically shown limitations in sample preparation and data repeatability below bubble point pressures. Accordingly, to improve the quality of subsurface models and the design of oil and gas extraction, transportation, and processing systems, there exists a need to quickly, efficiently, and accurately acquire viscosity data both above and below bubble point pressures.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system. The system includes a temperature control chamber with a temperature system to alter and monitor a temperature of the temperature control chamber and an electromagnetic viscometer (EMV) inside the temperature control chamber to measure a viscosity of a fluid. The system also includes a sample preparation cell within the temperature control chamber pressurized by a constant displacement pump outside the temperature control chamber. The sample preparation cell includes a stirrer; a first valve between a fluid supply reservoir and the sample preparation cell; a second valve between the sample preparation cell and the EMV, a venting fluid line between the sample preparation cell and a gas capturing system, and a venting fluid line to remove released gases from the sample preparation cell. The system further includes a controller to operate the sample preparation cell, temperature system, and EMV.

In one aspect, embodiments disclosed herein relate to a method for determining viscosity of a fluid using a pressure-volume-temperature (PVT) electromagnetic viscometer (EMV) system. The method includes receiving, by a sample preparation cell disposed within the PVT EMV system, the fluid from a fluid supply reservoir, and adjusting, under control of a controller configured to operate the sample preparation cell, temperature system, and EMV, a temperature of a temperature control chamber disposed within the PVT EMV system using the temperature system. The method further include, for each set pressure in a plurality of set pressures, where each set pressure in the plurality of set pressures is below a bubble point pressure of the fluid, adjusting a pressure of the fluid in the sample preparation cell to the set pressure, homogenizing the fluid by stirring the fluid with a stirrer disposed within the sample preparation cell, and degassing the fluid by removing released gases from the sample preparation cell though a venting fluid line in fluid communication with the sample preparation cell and a gas capturing system configured to remove released gases from the sample preparation cell. For each set pressure in a plurality of set pressures, the method still further includes transporting a volume of the fluid from the sample preparation cell to the EMV, measuring the viscosity of the volume of the fluid in the EMV, transmitting the viscosity measurement to the controller, and removing the volume of the fluid from the EMV. The method also includes planning a wellbore to penetrate a hydrocarbon reservoir based on the measured viscosities, wherein the planned wellbore comprises a planned wellbore path.

Other aspects and advantages of the claimed subject matter will be apparent from the following description and the appended claims.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural references unless the context clearly dictates otherwise. Thus, for example, reference to a "fluid sample" includes reference to one or more of such fluid samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

Figure 1:
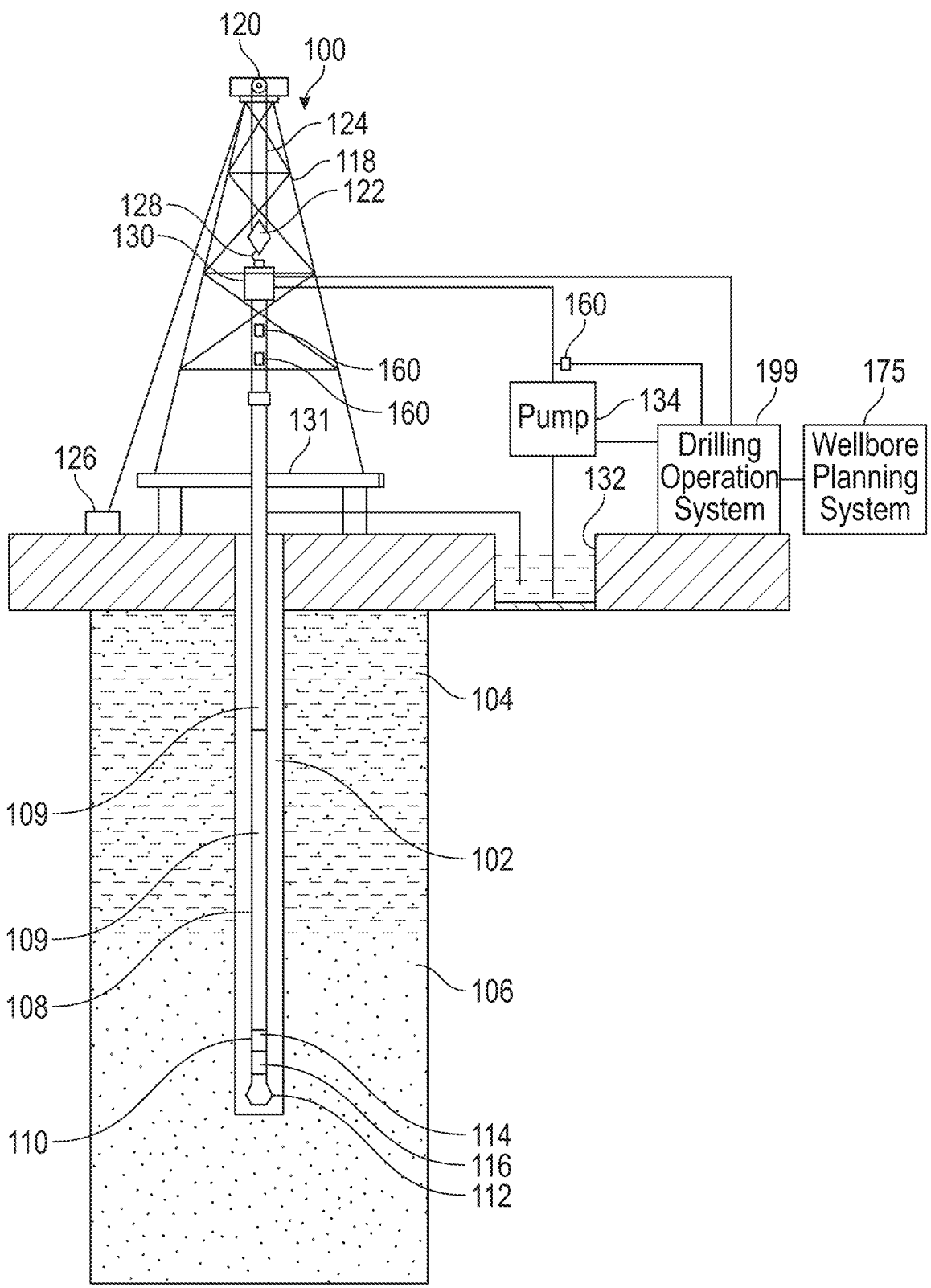
FIG. 1 depicts a well site and drilling system in accordance with one or more embodiments.

FIG. 1 depicts a simplified well site (100) with a drilling system. In general, well sites may be configured in a myriad of ways. Therefore, the illustrated well site (100) of FIG. 1 is not intended to be limiting with respect to the particular configuration of the drilling equipment. The well site (100) is depicted as being on land. In other examples, the well site (100) may be offshore, and drilling may be carried out with or without use of a marine riser. A drilling operation at well site (100) may include drilling a wellbore (102) into a subsurface including various formations (104, 106). The wellbore (102) may include a bored hole that extends from the surface into a target zone of the subsurface formations (104, 106), such as a reservoir. The subsurface formations (104, 106) may be categorized by various formation properties of interest, such as formation porosity, formation permeability, resistivity, density, water saturation, total organic content and the like. Properties of the subsurface formations (104, 106) may vary spatially.

For the purpose of drilling a new section of wellbore (102), a drill string (108) is suspended within the wellbore (102). The drill string (108) may include one or more drill pipes (109) connected to form conduit and a bottom hole assembly (BHA) (110) disposed at the distal end of the conduit. The BHA (110) may include a drill bit (112) to cut into the subsurface rock. The BHA (110) may include measurement tools, such as a measurement-while-drilling (MWD) tool (114) and logging-while-drilling (LWD) tool (116). Measurement tools (114, 116) may include sensors and hardware to measure downhole drilling parameters, and these measurements may be transmitted to the surface using any suitable telemetry system known in the art. By means of example, a LWD tool (116) commonly collects information about the properties of the subsurface formations (104, 106). As previously described, these may include, but are not limited to, the density, the porosity, and the resistivity of the subsurface formations (104, 106). The BHA (110) and the drill string (108) may include other drilling tools known in the art but not specifically shown.

The drill string (108) may be suspended in a wellbore (102) by a derrick (118). A crown block (120) may be mounted at the top of the derrick (118), and a traveling block (122) may hang down from the crown block (120) by means of a cable or drilling line (124). One end of the cable (124) may be connected to a draw works (126), which is a reeling device that may be used to adjust the length of the cable (124) so that the traveling block (122) may move up or down the derrick (118). The traveling block (122) may include a hook (128) on which a top drive (130) is supported.

The top drive (130) is coupled to the top of the drill string (108) and is operable to rotate the drill string (108). Alternatively, the drill string (108) may be rotated by means of a rotary table (not shown) on the drilling floor (131). Drilling fluid (commonly called mud) may be stored in a mud pit (132), and at least one pump (134) may pump the mud from the mud pit (132) into the drill string (108). The mud may flow into the drill string (108) through appropriate flow paths in the top drive (130) (or a rotary swivel if a rotary table is used instead of a top drive to rotate the drill string (108)).

In one implementation, a drilling operation system (199) may be disposed at or communicate with the well site (100). The drilling operation system (199) may control at least a portion of a drilling operation at the well site (100) by providing controls to various components of the drilling operation. In one or more embodiments, the drilling operation system (199) may receive data from one or more sensors (160) arranged to measure controllable parameters of the drilling operation. As a nonlimiting example, sensors (160) may be arranged to measure WOB (weight on bit), RPM (drill string rotational speed), GPM (flow rate of the mud pumps), and ROP (rate of penetration of the drilling operation).

Sensors (160) may be positioned to measure parameter(s) related to the rotation of the drill string (108), parameter(s) related to travel of the traveling block (122), which may be used to determine ROP of the drilling operation, and parameter(s) related to flow rate of the pump (134). For illustration purposes, sensors (160) are shown on drill string (108) and proximate mud pump (134). The illustrated locations of sensors (160) are not intended to be limiting, and sensors (160) could be disposed wherever drilling parameters need to be measured. Moreover, there may be many more sensors (160) than shown in FIG. 1 to measure various other parameters of the drilling operation. Each sensor (160) may be configured to measure a desired quantity.

During a drilling operation at the well site (100), the drill string (108) is rotated relative to the wellbore (102), and weight is applied to the drill bit (112) to enable the drill bit (112) to break rock as the drill string (108) is rotated. In some cases, the drill bit (112) may be rotated independently with a drilling motor (not shown). In other embodiments, the drill bit (112) may be rotated using a combination of the drilling motor and the top drive (130) (or a rotary swivel if a rotary table is used instead of a top drive to rotate the drill string (108)). While cutting rock with the drill bit (112), mud is pumped into the drill string (108).

The mud flows down the drill string (108) and exits into the bottom of the wellbore (102) through nozzles in the drill bit (112). The mud in the wellbore (102) then flows back up to the surface in an annular space between the drill string (108) and the wellbore (102) with entrained cuttings. The mud with the cuttings is returned to the mud pit (132) to be circulated back again into the drill string (108). Typically, the cuttings are removed from the mud, and the mud is reconditioned as necessary, before pumping the mud again into the drill string (108). In one or more embodiments, the drilling operation may be controlled by the drilling operation system (199).

As noted, the well site (100) provides well logs either through measurement tools (114, 116) while drilling or by post-drilling surveys such as a wireline tool (not shown). Furthermore, data about the subsurface formations (104, 106) near a well site (100) may be obtained by analyzing the entrained cuttings, as a function to drilling depth, exiting the wellbore (102). In addition to data acquired at a well-site, other methods for collecting data and characterizing subsurface formations (104, 106) exist. For example, a seismic survey may be conducted.

Prior to the commencement of drilling, a wellbore plan may be generated. The wellbore plan may include a starting surface location of the wellbore (102), or a subsurface location within an existing wellbore (102), from which the wellbore (102) may be drilled. Further, the wellbore plan may include a terminal location that may intersect with a target zone (e.g., a hydrocarbon-bearing formation) and a planned wellbore path from the starting location to the terminal location. In other words, the wellbore path may intersect a previously located hydrocarbon reservoir.

Typically, the wellbore plan is generated based on best available information at the time of planning from a geophysical model, geomechanical models encapsulating subterranean stress conditions, the trajectory of any existing wellbores (which it may be desirable to avoid), and the existence of other drilling hazards, such as shallow gas pockets, over-pressure zones, and active fault planes The wellbore plan may include wellbore geometry information such as wellbore diameter and inclination angle. If casing is used, the wellbore plan may include casing type or casing depths. Furthermore, the wellbore plan may consider other engineering constraints such as the maximum wellbore curvature ("dog-log") that the drill string (108) may tolerate and the maximum torque and drag values that the drilling system may tolerate.

A wellbore planning system (175) may be used to generate the wellbore plan. The wellbore planning system (175) may comprise one or more computer processors in communication with computer memory containing the geophysical and geomechanical models, information relating to drilling hazards, and the constraints imposed by the limitations of the drill string (108) and the drilling system. The wellbore planning system (175) may further include dedicated software to determine the planned wellbore path and associated drilling parameters, such as the planned wellbore diameter, the location of planned changes of the wellbore diameter, the planned depths at which casing will be inserted to support the wellbore (102) and to prevent formation fluids entering the wellbore, and the drilling mud weights (densities) and types that may be used during drilling the wellbore. The wellbore planning system (175) may be implemented using a computer such as computer 702 discussed below with reference to FIG. 7.

Figure 2:
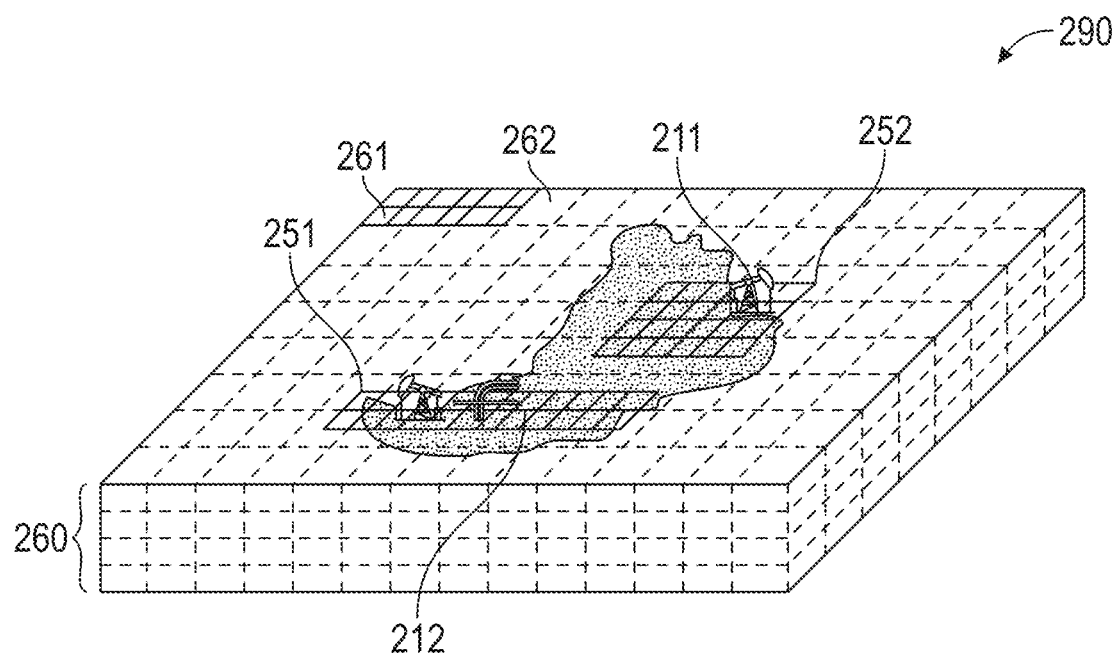
FIG. 2 depicts the discretization of a reservoir simulation in accordance with one or more embodiments.

Turning to FIG. 2, FIG. 2 shows the basis of a reservoir simulator in accordance with one or more embodiments. FIG. 2 shows a reservoir grid model (290) that corresponds to a geological region. The geological region may span multiple well sites (100) and a subsurface region of interest. The well sites (100) may include injection wells (212), which inject a fluid into the local subsurface formations (104, 106), or an extraction well (211). More specifically, the reservoir grid model (290) includes grid cells (261) that may refer to an original cell of a reservoir grid model as well as coarse grid blocks (262) that may refer to an amalgamation of original cells of the reservoir grid model. For example, a grid cell may be the case of a 1×1 block, where coarse grid blocks may be of sizes 2×2, 4×4, 8×8, etc. Both the grid cells (261) and the coarse grid blocks (262) may correspond to columns for multiple model layers (260) within the reservoir grid model (290).

Prior to performing a reservoir simulation, local grid refinement and coarsening (LGR) may be used to increase or decrease grid resolution in a certain area of reservoir grid model (290). For example, various reservoir properties, e.g., permeability, porosity or saturations, may correspond to a discrete value that is associated with a particular grid cell or coarse grid block. However, by using discrete values to represent a portion of a geological region, a discretization error may occur in a reservoir simulation. Thus, finer grids may reduce discretization errors as the numerical approximation of a finer grid is closer to the exact solution, however through a higher computational cost. As shown in FIG. 2, for example, the reservoir grid model (290) may include various fine-grid models (i.e., fine-grid model A (251), fine-grid model B (252)), that are surrounded by coarse block regions. Likewise, the original reservoir grid model (290) without any coarsening may also be a fine-grid model. In some embodiments, a reservoir grid model (or multiple reservoir grid models) may be used to preform reservoir simulations.

Generally, reservoir simulators solve a set of mathematical governing equations that represent the physical laws that govern fluid flow in porous, permeable media. For example, the flow of a single-phase slightly compressible oil with a constant viscosity and compressibility, equations that capture Darcy's law, the continuity condition, and the equation of state and may be written as:

$$\nabla^2 \rho(x, t) = \frac{\psi \mu c_t}{k} \frac{\partial \rho(x, t)}{\partial t}, \tag{1}$$

where $\rho$ represents fluid in the reservoir, x is a vector representing spatial position and t represents time. $\psi$, $\mu$, $c_t$, and k represent the physical and petrophysical properties of porosity, fluid viscosity, total combined rock and fluid compressibility, and permeability, respectively. $\nabla^2$ represents the spatial Laplace operator.

Additional and more complicated equations are required when more than one fluid, or more than one phase, e.g., liquid and gas, are present in the reservoir. Further, when the physical and petrophysical properties of the rocks and fluids vary as a function of position, the governing equations may not be solved analytically and must instead be discretized into a grid of cells or blocks (as depicted in FIG. 2). The governing equations must then be solved by one of a variety of numerical methods, such as, without limitation, explicit or implicit finite-difference methods, explicit or implicit finite element methods, or discrete Galerkin methods.

In some embodiments, a reservoir simulator comprises functionality for simulating the flow of fluids, including hydrocarbon fluids such as oil and gas, through a hydrocarbon reservoir composed of porous, permeable reservoir rocks in response to natural and anthropogenic pressure gradients. The reservoir simulator may be used to predict changes in fluid flow, including fluid flow into well penetrating the reservoir as a result of planned well drilling, and fluid injection and extraction. For example, the reservoir simulator may be used to predict changes in hydrocarbon production rate that would result from the injection of water into the reservoir from wells around the reservoirs periphery.

As stated, a reservoir simulator may account for, among other things, the porosity and hydrocarbon storage capacity of the subsurface formations (104, 106) and fluid transport pathways to predict the production rate of hydrocarbons of a well, or a set of wells, over their lifetime.

Under consideration of wellbore planning systems (175), reservoir simulators, and drilling operations, the need for accurate subsurface models and property estimation is selfevident. Accurate subsurface models are critical to reduce exploration risks, plan the location of well sites (100) (i.e., wellbore planning system), optimize reservoir production, improve reservoir characterization, best leverage existing discoveries, and better extend hydrocarbon recovery from existing wells. In particular, property estimation (e.g., viscosity) of the fluid extracted from a well is needed to calculate well inflow performance, and to determined fluid flow behavior as the fluid is surfaced and transported, such as through a pipeline, to processing facilities. Further, the determination of fluid properties is needed to determine the requirements of processing facilities.

Characterization of fluid behavior is in the subsurface is important to estimate the volume of hydrocarbons in the subsurface and further identify the recoverable components such as gas, condensates, volatile oil, and black oil. Further, the thermophysical properties of reservoir and other subsurface fluids are needed to define, describe, and predict (e.g., with a reservoir simulator) the reservoir processes and reservoir behavior as the reservoir is depleted.

Figure 3:
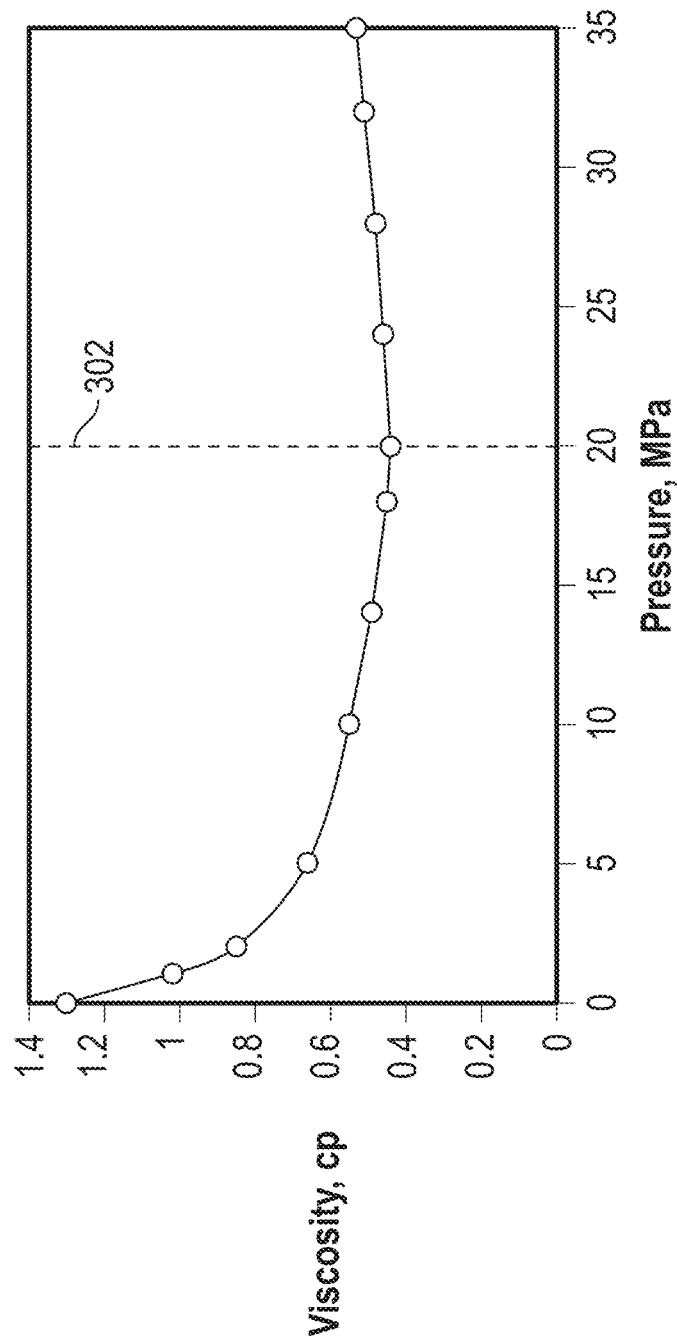
FIG. 3 depicts a plot relating viscosity to pressure for a sample fluid in accordance with one or more embodiments.

The thermophysical properties (e.g., viscosity, specific heat, conductivity) of reservoir fluids are dependent on pressure and temperature. For downhole applications, evaluation of fluid thermophysical properties, and other properties of the subsurface (e.g., porosity), may be complicated by the fact that the wellbore temperature and pressure changes substantially from the reservoir to the surface. Thus, fluids that are produced from the reservoir can experience a dramatic change in their thermophysical properties, including but not limited to their viscosity, as they are brought to the surface. It is noted that reservoir fluids often undergo a phase change both in the subsurface and when the fluids are surfaced. Another subsurface factor to consider is that subsurface fluids may experience a pressure less than the bubble point pressure of the fluids while surfacing and/or while in transit to a processing facility. The behavior and thermophysical properties of a fluid may change at the bubble point pressure of the fluid. As an example, FIG. 3 graphically depicts the viscosity of an example reservoir fluid over a variety of pressures at a fixed temperature. In FIG. 3, the bubble point pressure of the example reservoir fluid is depicted with a dashed line (302). As seen, starting at the pressure of 35 MPa, the viscosity of the example reservoir decreases with pressure until reaching the bubble point pressure (approximately 20 MPa). Further reduction in pressure beyond the bubble point pressure results in an increase in viscosity; a reversal of the fluid behavior. This is because upon reaching the bubble point pressure, gas is emitted from the example reservoir fluid such that, generally, heavier oils remain resulting in an increase in viscosity. One with ordinary skill in the art will recognize that the plot depicted in FIG. 3 is provided only as an example and should not be considered a limitation on the instant disclosure. In general, the thermophysical properties of a reservoir fluid (e.g., phase, viscosity) depend on the pressure, temperature, and volume of the fluid such tabulation of a property is multi-dimensional.

As emphasized by EQ. 1, reservoir models and production forecasting rely on an accurate determination of material properties, such as viscosity. Obtaining accurate and repeatable dynamic viscosity measurements of reservoir fluids at reservoir temperature and set pressures is crucial to reservoir fluid studies. The viscosity data aids in evaluating fluid behaviors and decisions on fluid transport mechanisms, the positioning of injection and production wells, and the design of flow lines.

In summary, to accurately support reservoir models, calculate flow rates, forecast production, and plan wells, among other activities, it is important to know the viscosity of the surfaced fluid as a function of wellbore depth (i.e., at various pressure and temperatures and transient conditions). Further, an accurate assessment of the viscosity of subsurface fluids is critical when considering how enhanced oil recovery (EOR) methods, if used, may impact the subsurface fluids.

In some situations, oil correlations can be used to determine the thermophysical properties of fluids over a variety of temperatures and pressures. General inputs used in oil correlation may include API oil gravity, initial solution gas-oil ratio from early production data, reservoir temperature, separator gas gravity temperature and pressure. Thermophysical properties determined from oil correlations, while useful, are known to deviate from measured values and therefore are associated with an uncertainty. For determining quantities like oil volume factor and dissolved gas-to-oil ratio, the calculation uncertainty usually lies withing 5% to 15%. However, oil correlations relating temperature and pressure to viscosity generally have an unacceptable level of uncertainty. In many cases, oil correlations for viscosity can be in error by an order of magnitude making such calculations unusable for reservoir simulations, production forecasting, etc. Consequently, the viscosity of reservoir fluids is generally determined through lab testing.

In a laboratory setting, samples of reservoirs fluids are evaluated with a viscometer to determine the fluid viscosity. Conventional high temperature and pressure viscometers currently used in the oil and gas industry for dynamic viscosity measurements of reservoir fluids have typically shown limitations in sample preparation and data repeatability below bubble point pressures. Namely, current viscometers may lack adequate sample preparation and data repeatability below bubble point pressures. Specifically, commercially available electromagnetic viscometers (EMV) and capillary viscometers used in the oil and gas industry for high temperature and pressure viscosity measurements do not have sample preparation cell and gas venting systems. Thus, the current industry systems have sample homogenizing and gas removal limitations that do not allow for accurate viscosity measurements below the bubble point pressure of the reservoir fluid.

As an example, Table I depicts the viscosity measurements of a given reservoir fluid sample using a conventional EMV. As shown in FIG. 3, for reservoir fluids, it is generally expected that starting at a high pressure that the viscosity of the reservoir fluid will decrease until the bubble point temperature and then begin to increase as the pressure is reduced further. As seen in Table I, the viscosity of the given reservoir fluid sample does, starting from a high pressure, decrease with pressure until the bubble point pressure (indicated at 1200 psia). However, in contrast to the correct result, the viscosity of the given reservoir fluid sample, as measured by the conventional EMV, continues to decrease as the pressure is reduced beyond the bubble point pressure.

TABLE I

Viscosity of a given reservoir fluid sample at various pressures measured using a conventional electromagnetic viscometer.

| Pressure (psia) | Viscosity (cP) |
| --- | --- |
| 4500 | 5.585 |
| 3500 | 5.571 |
| 2500 | 5.548 |
| 1500 | 5.534 |

TABLE I-continued

Viscosity of a given reservoir fluid sample at various pressures measured using a conventional electromagnetic viscometer.

| Pressure (psia) | Viscosity (cP) |
|---|---|
| 1200—bubble point | Diphasic fluid |
| 800 | 5.520 |
| 400 | 5.508 |
| 50 | 5.416 |

As emphasized by the incorrect results depicted in Table I obtained using an industry-standard viscometer, there exists a need to quickly, efficiently, and accurately acquire viscosity data of reservoir fluid samples both above and below bubble point pressures. Accurate viscosity data from reservoir fluid samples will improve the quality of subsurface models and the design of oil and gas extraction, transportation, and processing systems.

Generally, embodiments disclosed herein relate to a pressure-volume-temperature (PVT) electromagnetic viscometer (EMV) system and methods of use for the system to determine the viscosity of a reservoir fluid sample over a variety of temperatures and pressures, including pressures below the bubble point pressure of the fluid. Specifically, embodiments of the PVT EMV system disclosed herein may include the incorporation of a sample preparation cell that eliminates existing pressurized sample viscosity measurement challenges such as homogeneity and the venting of hydrocarbon gases released at set pressures below the bubble point pressure without affecting the remaining sample quality. Thus, embodiments of the PVT EMV system disclosed herein may have advantages including one or more of: achieving better repeatability or acquiring reliable viscosity measurement data with suitable sample volume (i.e., without requiring an undue or non-standard sample volume).

Figure 4:
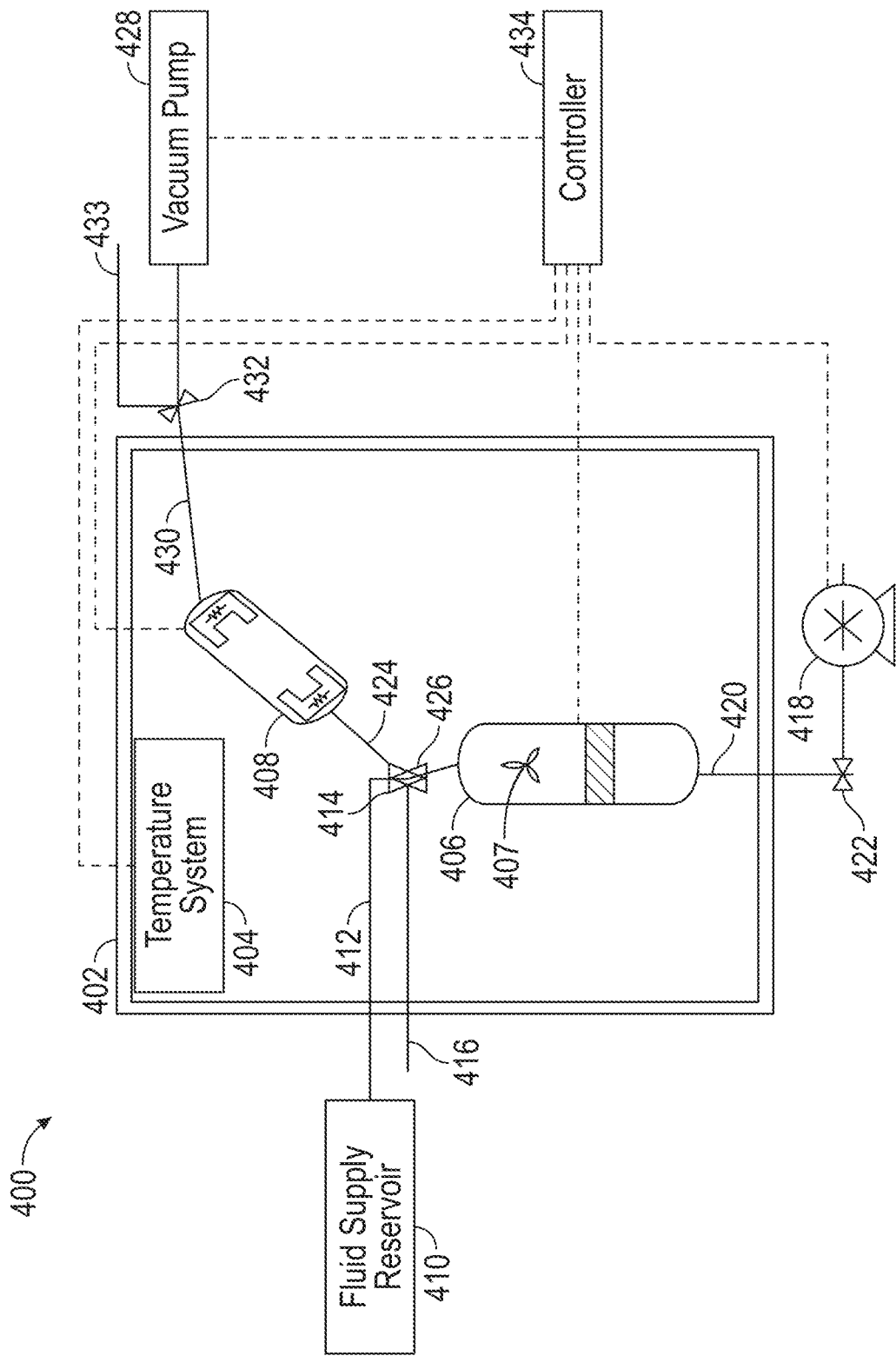
FIG. 4 depicts a pressure-volume-temperature (PVT) electromagnetic viscometer (EMV) system in accordance with one or more embodiments.

FIG. 4 depicts the pressure-volume-temperature (PVT) electromagnetic viscometer (EMV) system (400), in accordance with one or more embodiments. As seen in FIG. 4, the PVT EMV system (400) includes a temperature control chamber (402). The temperature control chamber (402) is insulated to provide a stable thermal environment. In one or more embodiments, the temperature control chamber (402) is outfitted with one or more glass panels or windows to allow for visual inspection of components contained within the temperature control chamber (402) without disturbing the thermal environment maintained by the temperature control chamber (402). The temperature control chamber (402) includes a temperature system (404). In one or more embodiments, the temperature system (404) includes a heating device, such as an air heater or a heating element, to heat the air and components within the temperature control chamber (402) to a desired temperature. In one or more embodiments, the temperature system (404) further includes a temperature sensor (e.g., thermocouple) and a temperature transmitter, where the temperature transmitter can transmit the temperature of the temperature control chamber (402), as sensed by the temperature sensor, to an external device and/or a control device. In some instances, the temperature sensor and the temperature transmitter may be considered the same device. That is, one or more devices used in the temperature system (404) may be capable of both sensing and transmitting functionalities.

Continuing with FIG. 4, embodiments of the PVT EMV system (400) may further include a sample preparation cell (406), including a stirrer (407), and an electromagnetic viscometer (EMV) (408) disposed within the temperature control chamber (402). Because the sample preparation cell (406) and the EMV (408) are disposed within the temperature control chamber (402), the sample preparation cell (406), the EMV (408), and any fluid they may contain will, under steady state conditions, be at the internal temperature of the temperature control chamber (402).

Embodiments of the PVT EMV system (400) may further include a fluid supply reservoir (410) disposed external to the temperature control chamber (402). In one or more embodiments, the fluid supply reservoir (410) is a titanium cylinder. The fluid supply reservoir (410) contains a reservoir fluid (or any subsurface fluid). The reservoir fluid may be acquired from a wellbore, a fracture in a formation, a body of water or oil or mixture of materials, or other void in a subterranean formation that is large enough from which to collect a sample. Without loss of generality, the reservoir fluid may contain solid particles such as sand, salt crystals, proppant, solid acids, solid or viscous hydrocarbon, viscosity modifiers, weighing agents, completions residue, or drilling debris. Further, the reservoir fluid may contain water (e.g., salt water), hydrocarbons, drilling mud, emulsions, fracturing fluid, and other chemical constituents often used in drilling operations such as viscosifiers, surfactants, and/or dissolved gases. In one or more embodiments, the fluid supply reservoir (410) is hydraulically connected to the sample preparation cell (406) by a first fluid line (412) that penetrates the temperature control chamber (402). In one or more embodiments, the entry point of the first fluid line (412) into the temperature control chamber (402) is hermetically sealed and well insulted such that air within the temperature control chamber (402) cannot escape. With the first fluid line (412), reservoir fluid from the fluid supply reservoir (410) can be transported to the sample preparation cell (406). Movement of reservoir fluid from the fluid supply reservoir (410) to the sample preparation cell (406) may be managed, at least in part, with a first valve (414) disposed along the first fluid line (412). In one or more embodiments, the first valve (414) can be "opened" or "closed", allowing for or preventing movement of reservoir fluid, respectively, through the first fluid line (412). In one or more embodiments, the PVT EMV system further includes a high-pressure filter (not shown) disposed on the first fluid line (412). The high-pressure filter removes particulates from the reservoir fluid.

Embodiments of the PVT EMV system (400) may further include a venting fluid line (416) that hydraulically connects the sample preparation cell (406) to a gas capturing system (not shown) external to the temperature control chamber (402). As will be described in greater detail below, the sample preparation cell (406) can vent gasses released from a reservoir fluid contained in the sample preparation cell (406) to the gas capturing system. In one or more embodiments, the gas capturing system is pressurized. In one or more embodiments, a gas capturing system is not employed such that the venting fluid line vents released gases directly to the external environment. In one or more embodiments, the movement of released gases from the sample preparation cell (406) is managed, at least in part, with the first valve (414). That is, in one or more embodiments, the first valve may simultaneously and independently manage the states of the first fluid line (412) and the venting fluid line (416). The sample preparation cell (406) further includes a mixer (not shown) that can mix, or otherwise stir, reservoir fluid contained within the sample preparation cell (406).

Embodiments of the PVT EMV system (400) may further include a constant displacement pump (418) external to the temperature control chamber (402). The constant displacement pump (418) according to the embodiment shown is hydraulically connected to the sample preparation cell (406) with a pressure fluid line (420) that may be opened or closed using pressure line valve (422). The constant displacement pump (418) can pressurize any reservoir fluid contained by the sample preparation cell (406). The sample preparation cell (406) is further hydraulically connected to the EMV (408) by a second fluid line (424). A second valve (426) is disposed on the second fluid line (424) that can control whether the second fluid line (424) is open or closed.

In one or more embodiments, the PVT EMV system (400) further includes a vacuum pump (428) disposed externally to the temperature control chamber (402). The vacuum pump (428) is hydraulically connected to the EMV (408) by a third fluid line (430). A third valve (432) is disposed on the third fluid line (430). In one or more embodiments, the third valve (432) further hydraulically connects the EMV (408) to the environment, or a post-test sample collection system (not shown), via sample removal line (433). That is, the third fluid line (430) and the sample removal line (433), in coordination with the third valve (432) can be used to remove reservoir fluid from the EMV (408), where, in some situations, the removal of the reservoir fluid from the EMV (408) is aided by the vacuum pump (428).

Finally, in one or more embodiments, the PVT EMV system (400) further includes a controller (434). The controller (434) may include one or more controllers and/or edge computing devices. In one or more embodiments, the controller (434) can receive, process, and record signals generated by the temperature system (404), sample preparation cell (406), EMV (408), constant displacement pump (418), and vacuum pump (428). Further, in one or more embodiments, the controller (434) can transmit control signals to alter the operation of the temperature system (404), sample preparation cell (406), EMV (408), constant displacement pump (418), and vacuum pump (428). FIG. 4 depicts the connectivity the controller (434) to various other components of the PVT EMV system (400) using dashed lines. In general, the connection of the controller (434) to components of the PVT EMV system (400) may be wired or wireless. In one or more embodiments, the controller (434) is further connected to, and capable of receiving and transmitting signals to, one or more of the valves of the PVT EMV system (400) (i.e., the first valve (414), the second valve (426), the third valve (432), pressure line valve (422)). In these embodiments, the controller (434) can identify and control the state (e.g., open or closed) of the valves of the PVT EMV system (400). It is noted that to promote clarity, connection lines between the controller (434) and valve of the PVT EMV system (400) are not drawn in FIG. 4.

Figure 5:
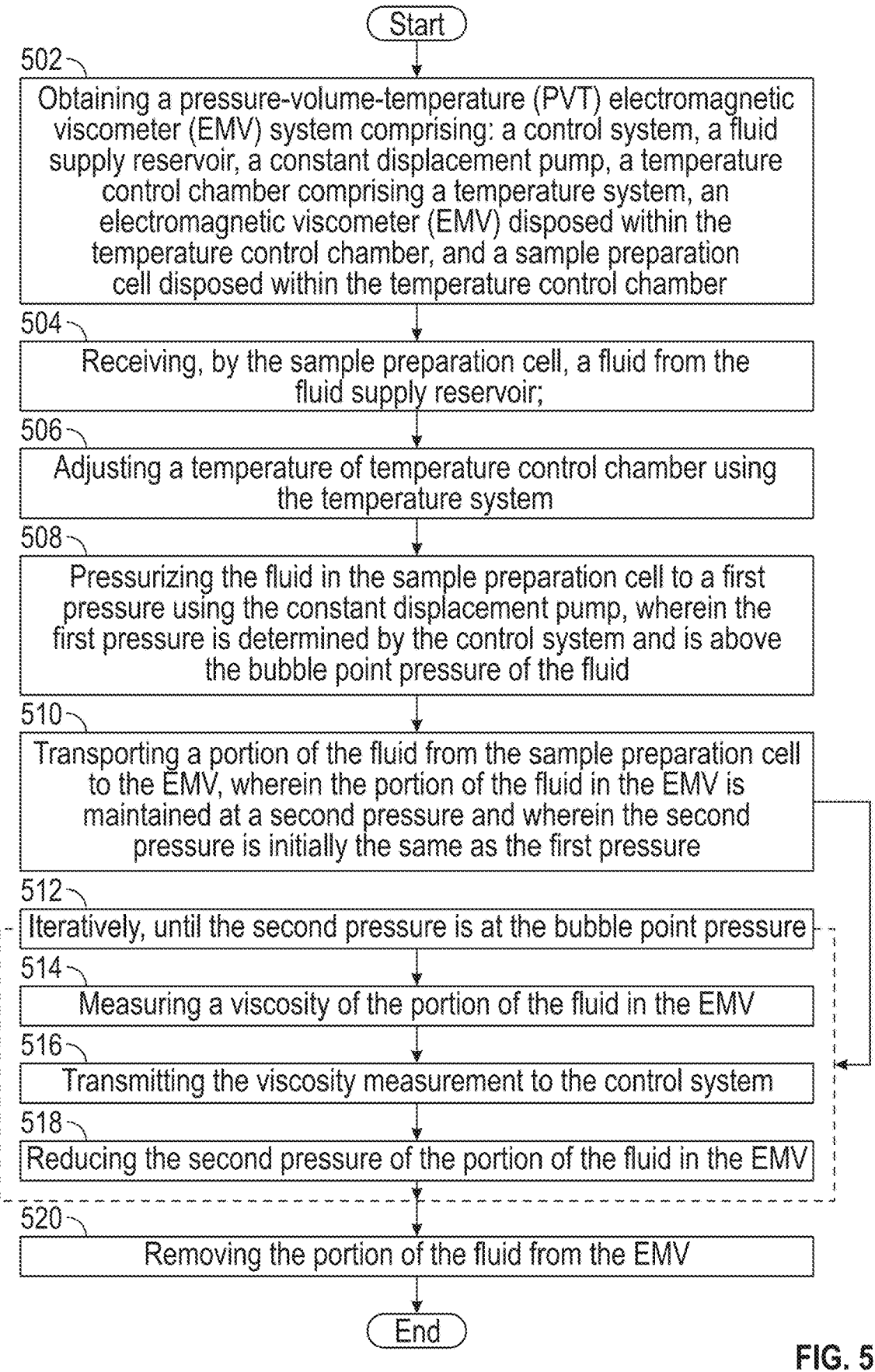
FIG. 5 depicts a flowchart in accordance with one or more embodiments.

Turning to FIG. 5, FIG. 5 depicts a method for using the PVT EMV system (400) described herein, in accordance with one or more embodiments. In particular, FIG. 5 depicts a method for using the PVT EMV system (400) to measure the viscosity of a reservoir fluid above the bubble point pressure of the reservoir fluid. In Block 502, a PVT EMV system (400), as described above and depicted in FIG. 4 is provided. The PVT EMV system (400) includes, but is not limited to: a controller; a fluid supply reservoir; a constant displacement pump; a temperature control chamber including a temperature system; an electromagnetic viscometer (EMV) disposed within the temperature control chamber; and a sample preparation cell disposed within the temperature control chamber.

In Block 504, a fluid from the fluid supply reservoir (410) is transported from the fluid supply reservoir (410) to the sample preparation cell (406) by use of the first fluid line (412) and the first valve (414). In one or more embodiments, 40 cc of fluid is charged in the sample preparation cell (406). Once the fluid is charged in the sample preparation cell (406), the first valve (414) is closed. In Block 506, the temperature of the temperature control chamber (402) is adjusted to a desired set temperature using the temperature system (404). Thus, viscosity measurements may be acquired at various temperatures by adjusting the temperature of the temperature control chamber (402) and repeating the remaining processes depicted in FIG. 5. In Block 508, the fluid, now contained in the sample preparation cell (406) is pressurized to a first pressure. The pressurization is performed using the constant displacement pump (418). In one or more embodiments, the pressure is controlled by the controller (434). The first pressure is greater than the bubble point pressure of the fluid. One with ordinary skill in the art will recognize that adjustments of temperature and pressure are not instantaneous. As such, it is fully understood that upon making an adjustment to either the temperature of the temperature control chamber (402) or the pressure of the sample preparation cell (406), sufficient time is allowed for the fluid in the sample preparation cell (406) to reach steady state conditions. Once the pressure and temperature of the fluid in the sample preparation cell (406) is stabilized (i.e., steady state at the desired temperature and pressure), in Block 510 a portion of the fluid is transported from the sample preparation cell (406) to the EMV (408). In one or more embodiments, the portion of the fluid is transported through the second fluid line (424) by operating the second valve (426) (while ensuring the first valve (414) is shut), after which the second valve (426) is closed. The amount of fluid contained in the portion of the fluid transported to the EMV (408) is according to the requirements and capacity of the EMV (408). The portion of fluid in the EMV (408) is maintained at a second pressure. Upon initial transport of the portion of the fluid from the sample preparation cell (406) to the EMV (408), the second pressure is the same as the first pressure.

Block 512 of FIG. 5 encloses Blocks 514, 516, and 518 and represents an iterative process. In particular, as depicted in Block 512, the processes of Blocks 514, 516, and 518 are performed iteratively until the second pressure (i.e., the pressure of the portion of the fluid in the EMV (408)) is reduced to the bubble point pressure of the fluid. In Block 514, the EMV (408) is used to measure the viscosity of the portion of the fluid. In Block 516, the measured viscosity is transmitted to, and recorded by, the controller (434). In Block 518, the second pressure is reduced. In one or more embodiments, the second pressure is reduced by venting or removing some of the portion of the fluid in the EMV (408) from the EMV (408) and to the post-test sample collection system. Removal and/or venting of some of the portion of the fluid in from the EMV (408) is performed by temporally opening the third valve (432), allowing the fluid to move from the EMV (408) to the post-test sample collection system through the third fluid line (430) and the sample removal line (433). In one or more embodiments, the pressure reduction is discrete and the discrete change in pressure is determined by a user. Once the second pressure has stabilized, the viscosity of the portion of the fluid is measured, transmitted, and recorded at the newly reduced pressure according to Blocks 514 and 516. Once the second pressure has been reduced to the bubble point pressure of the fluid, the iterative process enclosed by Block 512 is terminated. In Block 520, the portion of the fluid is completely removed from the EMV (408). In one or more embodiments, the complete removal of the portion of the fluid from the EMV (408) is facilitated by the vacuum pump (428), where operation of the third valve (432) allows the vacuum pump (428) to pull (or suck) all of the portion of the fluid from the EMV (408) to the post-test sample collection system through the third fluid line (430) and the sample removal line (433). It is noted that all processes contained by Blocks 504 through 520 may be controlled, and/or performed automatically, by the controller (434) of the PVT EMV system (400).

Figure 6:
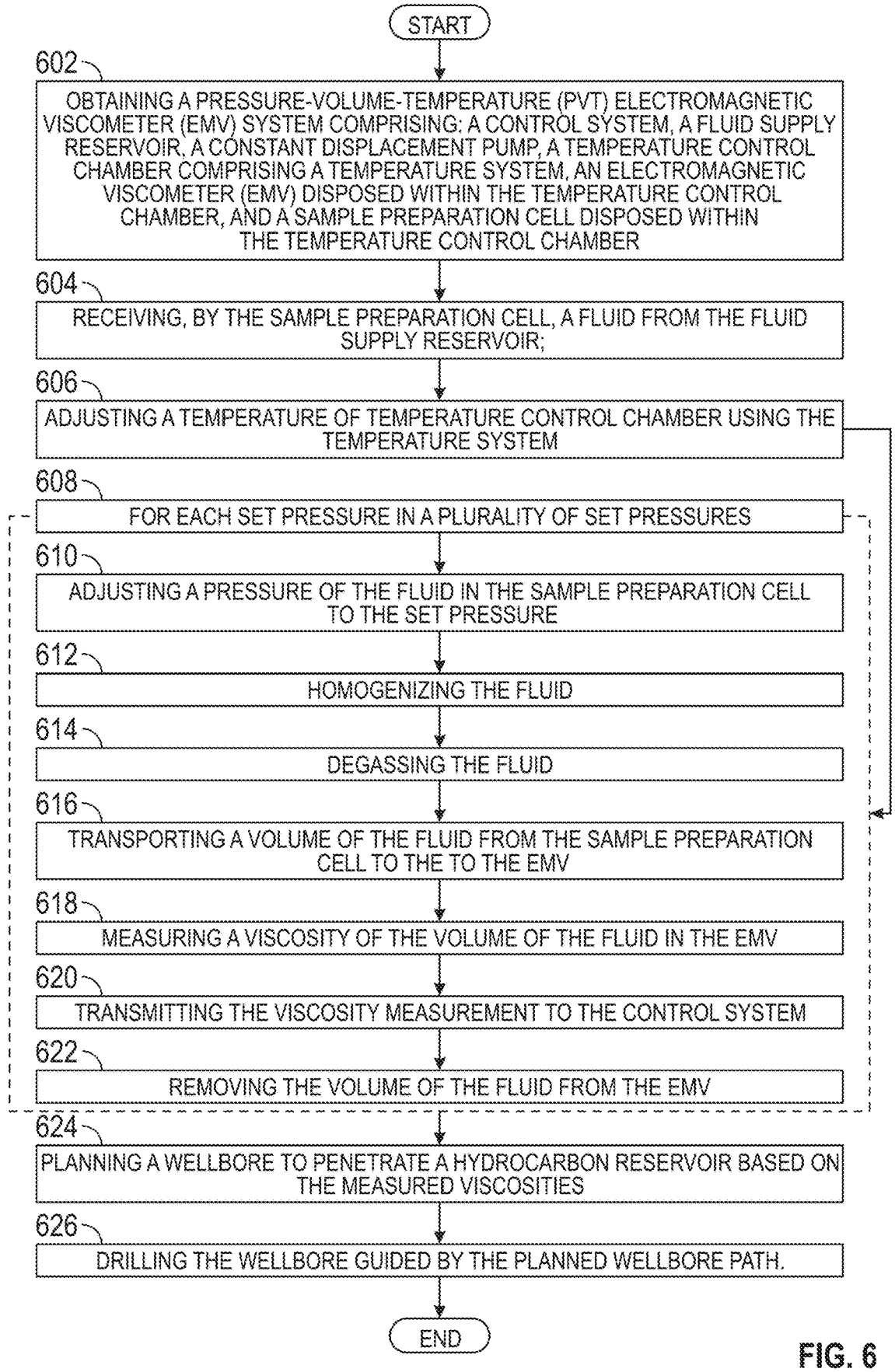
FIG. 6 depicts a flowchart in accordance with one or more embodiments.

FIG. 6 depicts a method for using the PVT EMV system (400) described herein, in accordance with one or more embodiments. In particular, FIG. 6 depicts a method for using the PVT EMV system (400) to measure the viscosity of a reservoir fluid below the bubble point pressure of the reservoir fluid. In Block 602, a PVT EMV system (400), as described above and depicted in FIG. 4 is provided. The PVT EMV system (400) includes, but is not limited to: a controller; a fluid supply reservoir; a constant displacement pump; a temperature control chamber including a temperature system; an electromagnetic viscometer (EMV) disposed within the temperature control chamber; and a sample preparation cell disposed within the temperature control chamber.

In Block 604, a fluid from the fluid supply reservoir (410) is transported from the fluid supply reservoir (410) to the sample preparation cell (406) by use of the first fluid line (412) and the first valve (414). In one or more embodiments, 40 cc of fluid is charged in the sample preparation cell (406). Once the fluid is charged in the sample preparation cell (406), the first valve (414) is closed. In Block 606, the temperature of the temperature control chamber (402) is adjusted to a desired set temperature using the temperature system (404). Thus, viscosity measurements may be acquired at various temperatures by adjusting the temperature of the temperature control chamber (402) and repeating the remaining processes depicted in FIG. 6.

Block 608 of FIG. 6 encloses Blocks 610 through 622 and represents an iterative process. Block 608 defines a plurality of set pressures, where each pressure in the plurality of set pressures is at or below the bubble point pressure of the fluid. As such, the processes of Blocks 610 through 622 are performed for each set pressure in the plurality of set pressure according to Block 608. In Block 610, the fluid, now contained in the sample preparation cell (406) is pressurized to a set pressure, where the set pressure is determined by the current iteration (Block 608). The pressurization is performed using the constant displacement pump (418). In one or more embodiments, the pressure is controlled by the controller (434). One with ordinary skill in the art will recognize that adjustments of temperature and pressure are not instantaneous. As such, it is fully understood that upon making an adjustment to either the temperature of the temperature control chamber (402) or the set pressure of the sample preparation cell (406), sufficient time is allowed for the fluid in the sample preparation cell (406) to reach steady state conditions. Once the pressure and temperature of the fluid in the sample preparation cell (406) is stabilized (i.e., steady state at the desired temperature and pressure), in Block 612 the fluid is homogenized. In one or more embodiments, homogenization of the fluid is performed by mixing or stirring the fluid in the sample preparation cell (406) with a stirrer (407). In Block 614, the fluid is degassed. Given that the set pressure is below the bubble point pressure of the fluid, gases are expected to be released from the fluid. In one or more embodiments, released gases are removed from the sample preparation chamber through the venting fluid line (416). In one or more embodiments, the venting fluid line (416) is hydraulically connected to a gas capturing system external to the temperature control chamber (402). In one or more embodiments, the gas capturing system is at the same pressure (or slightly below) as the set pressure such that released gases can be evacuated from the sample preparation cell (406) without alerting the set pressure maintained in the sample preparation cell (406). In one or more embodiments, released gases are vented through the venting fluid line (416) by operation of the first valve (414).

In Block 616, once degassed, a volume of the fluid is transported from the sample preparation cell (406) to the EMV (408). In one or more embodiments, the volume of the fluid is transported through the second fluid line (424) by operating the second valve (426) (while ensuring the first valve (414) is shut). The amount of fluid contained in the volume of fluid transported to the EMV (408) is according to the requirements and capacity of the EMV (408). The volume of fluid in the EMV (408) is maintained at the given set pressure by shutting the second valve (426). In Block 618, the EMV (408) is used to measure the viscosity of the volume of fluid. In Block 620, the measured viscosity is transmitted to, and recorded by, the controller (434). In Block 622, the volume of fluid is completely removed from the EMV (408). In one or more embodiments, the complete removal of the volume of fluid from the EMV (408) is facilitated by the vacuum pump (428), where operation of the third valve (432) allows the vacuum pump (428) to pull (or suck) all of the portion of the fluid from the EMV (408) to the post-test sample collection system through the third fluid line (430) and the sample removal line (433). It is noted that all processes contained by Blocks 610 through 622 may be controlled, and/or performed automatically, by the controller (434) of the PVT EMV system (400).

Once a volume of fluid has been tested and removed from the EMV (408) at each set pressure in the plurality of set pressures (Block 608), the processes of FIG. 6 proceed to Block 624. In Block 624, the measured and recorded viscosity values are used to plan a wellbore to penetrate a hydrocarbon reservoir. In one or more embodiments, the viscosity measurements may inform a subsurface model or reservoir simulator. Thus, the output of the reservoir simulator (e.g., production forecasting, well performance metrics, etc.), based on the viscosity data obtained with the PVT EMV system (400) described herein, may inform well placement and wellbore planning. Finally, in Block 626, a wellbore is drilled guided by the planned wellbore path determined in Block 624.

One with ordinary skill in the art will recognize that the methods depicted in FIGS. 5 and 6 may be performed in various combinations. For example, in one or more embodiments, the method of FIG. 5 is performed and then the method of FIG. 6 can be directly started at Block 608 without the need for Blocks 602 through 606. That is, in one or more embodiments, measurements of the viscosity of a fluid below the bubble point pressure of the fluid may be performed immediately after measurements of viscosity above the bubble point pressure of the fluid without needing to receive additional fluid from the fluid supply reservoir (410) or re-adjust the set temperature of the temperature control chamber (402). Thus, the PVT EMV system (400) described herein provides quick, efficient, and accurate viscosity data over a wide range of pressures, including both above and below the bubble point pressure of the tested fluid.

While the various blocks in FIGS. 5 and 6 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Figure 7:
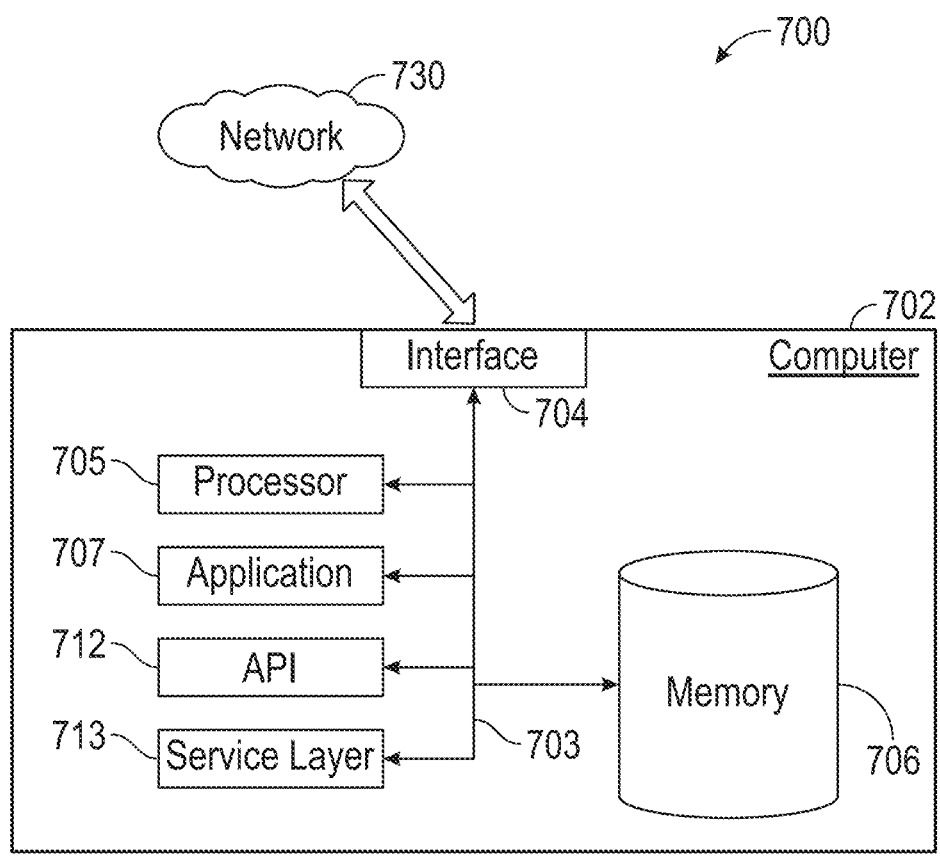
FIG. 7 depicts a system in accordance with one or more embodiments.

FIG. 7 shows a system in accordance with one or more embodiments. FIG. 7 depicts a block diagram of the computer system (702) used to provide computational functionalities associated with the methods and procedures as described in this disclosure, according to one or more embodiments (e.g., the controller (434)). The illustrated computer (702) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a Graphical User Interface (GUI).

The computer (702) can serve in a role as a client, network component, a server, a database or other persistency, or any other component (or a combination of roles) of a computer system for performing the subject matter described in the instant disclosure. The illustrated computer (702) is communicably coupled with a network (730). In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702)) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or another suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (704) includes logic encoded in software or hardware (or a combination of software and hardware) and operable to communicate with the network (730). More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components, such as computer executable instructions, (or a combination of both) that can be connected to the network (730). The memory (706) may be non-transitory computer readable memory. For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), wherein each computer (702) communicates over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

In summary, advantages of embodiments of this disclosure may include one or more of the following: better sample mixing procedure; increases sample stabilization; reduction in measurement uncertainties associated with reservoir fluid viscosity measurements of both monophasic and diphasic hydrocarbon liquids; and removal of liberated hydrocarbon gases below saturation pressures. As such, embodiments of the PVT EMV system (400) disclosed herein may eliminate sample preparation challenges plaguing industry standard and state-of-the-art viscometers.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A system comprising:
  a temperature control chamber comprising a temperature system configured to alter and monitor a temperature of the temperature control chamber;
  an electromagnetic viscometer (EMV) disposed within the temperature control chamber, where in the EMV is configured to measure a viscosity of a fluid;
  a sample preparation cell disposed within the temperature control chamber configured to be pressurized by a constant displacement pump external to the temperature control chamber, the sample preparation cell comprising a stirrer;
  a first valve in fluid communication with a fluid supply reservoir external to the temperature control chamber and the sample preparation cell;
  a second valve in fluid communication with the sample preparation cell and the EMV;
  a venting fluid line in fluid communication with the sample preparation cell and a gas capturing system, wherein the venting fluid line is configured to remove released gases from the sample preparation cell;
  a controller configured to operate the sample preparation cell, temperature system, and EMV.

2. The system of claim 1, further comprising: a third valve in fluid communication with the EMV; and a vacuum pump external to the temperature control chamber, wherein the vacuum pump is configured to remove the fluid from the EMV.

3. The system of claim 2, further comprising a pressure line valve operable to adjust a pressure supplied to the sample preparation cell by the constant displacement pump.

4. The system of claim 3, wherein the controller is configured to control a state of the first valve, second valve, third valve, and pressure line valve.

5. The system of claim 1,
  wherein the first valve is operable to prevent or allow transmission of the fluid from the fluid supply reservoir and the sample preparation cell; and
  wherein the second valve is operable to prevent or allow the transmission of the fluid from the sample preparation cell to the EMV.

6. The system of claim 1,
  wherein the first valve is operable to prevent or allow transmission of the released gases from the sample preparation cell to the gas capturing system through the venting fluid line.

7. The system of claim 1, further comprising:
  a temperature sensor disposed within the temperature control chamber;
  a temperature transmitter configured to transmit the temperature of the temperature control chamber, as measured by the temperature sensor, to the controller;
  a pressure sensor configured to measure a pressure of the sample preparation cell; and
  a pressure transmitter configured to transmit the pressure, as measured by the pressure sensor, to the controller.

8. The system of claim 7, wherein the controller is configured to:
  receive a pressure signal from the pressure transmitter;
  receive a temperature signal from the temperature transmitter;
  receive the viscosity measurement from the EMV; and
  transmit a plurality of control signals to control the temperature and pressure of a fluid within the EMV and to circulate the fluid throughout the temperature control chamber.

9. The system of claim 8, wherein the controller is further configured to record the viscosity measurement.

10. A method for determining viscosity of a fluid using a pressure-volume-temperature (PVT) electromagnetic viscometer (EMV) system, comprising:
  receiving, by a sample preparation cell disposed within the PVT EMV system, the fluid from a fluid supply reservoir;
  adjusting, under control of a controller configured to operate the sample preparation cell, temperature system, and EMV, a temperature of a temperature control chamber disposed within the PVT EMV system using the temperature system;
  executing, for each set pressure in a plurality of set pressures, the following steps, wherein each set pressure in the plurality of set pressures is below a bubble point pressure of the fluid:
    adjusting a pressure of the fluid in the sample preparation cell to the set pressure,
    homogenizing the fluid by stirring the fluid with a stirrer disposed within the sample preparation cell,
    degassing the fluid by removing released gases from the sample preparation cell though a venting fluid line in fluid communication with the sample preparation cell and a gas capturing system configured to remove released gases from the sample preparation cell,
    transporting a volume of the fluid from the sample preparation cell to the EMV,
    measuring the viscosity of the volume of the fluid in the EMV,
    transmitting the viscosity measurement to the controller, and removing the volume of the fluid from the EMV; and planning a wellbore to penetrate a hydrocarbon reservoir based on the measured viscosities,
  wherein the planned wellbore comprises a planned wellbore path.

11. The method of claim 10, further comprising:

pressurizing the fluid in the sample preparation cell to a first pressure using a constant displacement pump, wherein the first pressure is determined by the controller and is above the bubble point pressure of the fluid;

transporting a portion of the fluid from the sample preparation cell to the to the EMV, wherein the portion of the fluid in the EMV is maintained at a second pressure and wherein the second pressure is initially equal to the first pressure;

iteratively, until the second pressure is at the bubble point pressure:
  measuring a viscosity of the portion of the fluid in the EMV,
  transmitting the viscosity measurement to the controller, and
  reducing the second pressure of the portion of the fluid in the EMV; and removing the portion of the fluid from the EMV.

12. The method of claim 10, further comprising:

measuring the temperature of the temperature control chamber with a temperature sensor disposed within the temperature control chamber;

transmitting the measured temperature with a temperature transmitter to the controller;

measuring the pressure of the sample preparation cell with a pressure sensor; and transmitting the measured pressure with a pressure transmitter to the controller.

13. The method of claim 10, further comprising:

transmitting, from the controller, a plurality of control signals to control the temperature and pressure of the fluid and to circulate the fluid throughout the temperature control chamber.

14. The method of claim 13, further comprising circulating the fluid by a plurality of valves under the operation of the controller.

15. The method of claim 10, further comprising drilling the wellbore guided by the planned wellbore path.

* * * * *